United States Patent [19]
Todd et al.

[11] 4,282,881
[45] Aug. 11, 1981

[54] MANOMETER FOR INFUSION APPARATUS

[75] Inventors: Robert J. Todd; Gregg H. Smith, both of Salt Lake City; Gordon S. Reynolds, Bountiful, all of Utah

[73] Assignee: Sorenson Research Co., Inc., Salt Lake City, Utah

[21] Appl. No.: 37,614

[22] Filed: May 10, 1979

[51] Int. Cl.³ .............................................. A61B 5/02
[52] U.S. Cl. ................................. 128/674; 128/675; 73/748
[58] Field of Search ............... 128/214 E, 214 F, 650, 128/674, 675, DIG. 12, DIG. 13; 73/708, 747, 748, 714

[56] References Cited

U.S. PATENT DOCUMENTS

| | | | |
|---|---|---|---|
| 1,423,565 | 7/1922 | Kemp | 73/747 |
| 2,017,435 | 10/1935 | Ey | 73/747 |
| 2,361,628 | 10/1944 | Howard | 73/748 |
| 2,842,123 | 7/1958 | Rundhaug | 128/214 |
| 3,233,457 | 2/1966 | Martinez | 73/198 |
| 3,435,819 | 4/1969 | Reynolds et al. | 128/674 |
| 3,460,526 | 8/1969 | McKirdy et al. | 128/674 |
| 3,533,400 | 10/1970 | Palich | 128/674 |
| 3,610,046 | 10/1971 | Lissau | 73/747 X |
| 3,610,230 | 10/1971 | Andersen | 128/674 |
| 3,690,318 | 9/1972 | Gorsuch | 128/214 E |
| 3,730,168 | 5/1973 | McWhorter | 128/674 X |
| 3,807,389 | 4/1974 | Miller et al. | 128/674 |
| 3,850,348 | 11/1974 | Bessot et al. | 128/214 E X |
| 3,980,082 | 9/1976 | Miller | 128/214 R |
| 4,043,332 | 8/1977 | Metcalf | 128/214 E |

Primary Examiner—Kyle L. Howell
Attorney, Agent, or Firm—Fox, Edwards & Gardiner

[57] ABSTRACT

A manometer for measuring the hydrodynamic pressure of fluids parenterally administered to a patient. The manometer includes a transparent housing which has a passageway formed in the housing that accommodates continuous flow of fluid therethrough. A pressure measuring chamber is formed in the housing and one end of the pressure measuring chamber is in fluid communication with the passageway. The other end of the pressure measuring chamber communicates with an enclosed air space. The fluid flowing through the passageway enters the pressure measuring chamber and rises to a level which is dependent upon the pressure of the fluid flowing through the passageway. Markings are provided on the housing of the manometer which permit the pressure exerted on the fluid flowing through the passageway to be read directly from the level of the fluid in the pressure measuring chamber. In one embodiment of the manometer, the enclosed air space may be adjusted so that the manometer may be normalized for use at any one of several different altitudes. A valve is provided so that the enclosed air space may be vented to the ambient atmosphere when it is desired to set the pressure reading to zero. In another embodiment of the manometer, the pressure measuring chamber is provided with a progressively decreasing cross-sectional flow area from its bottom to its top so that the pressure may be read in a linear fashion.

35 Claims, 8 Drawing Figures

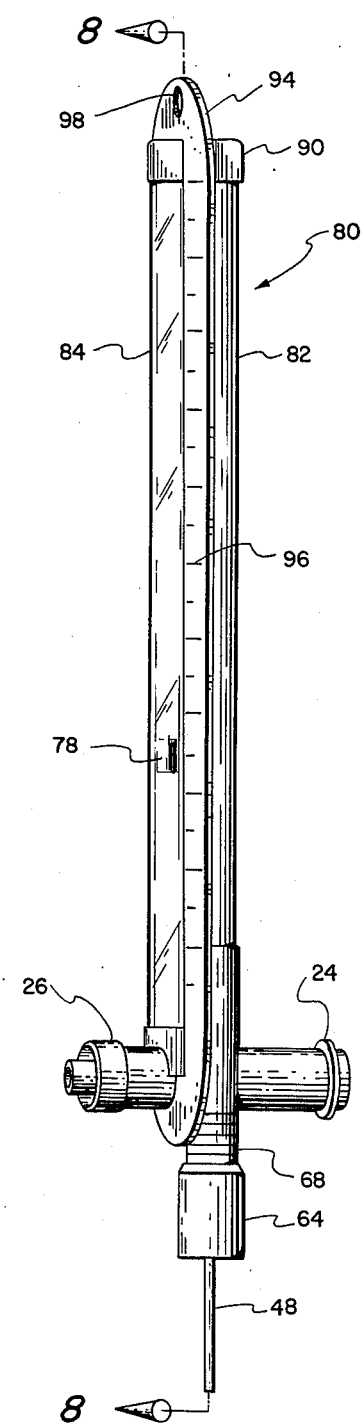
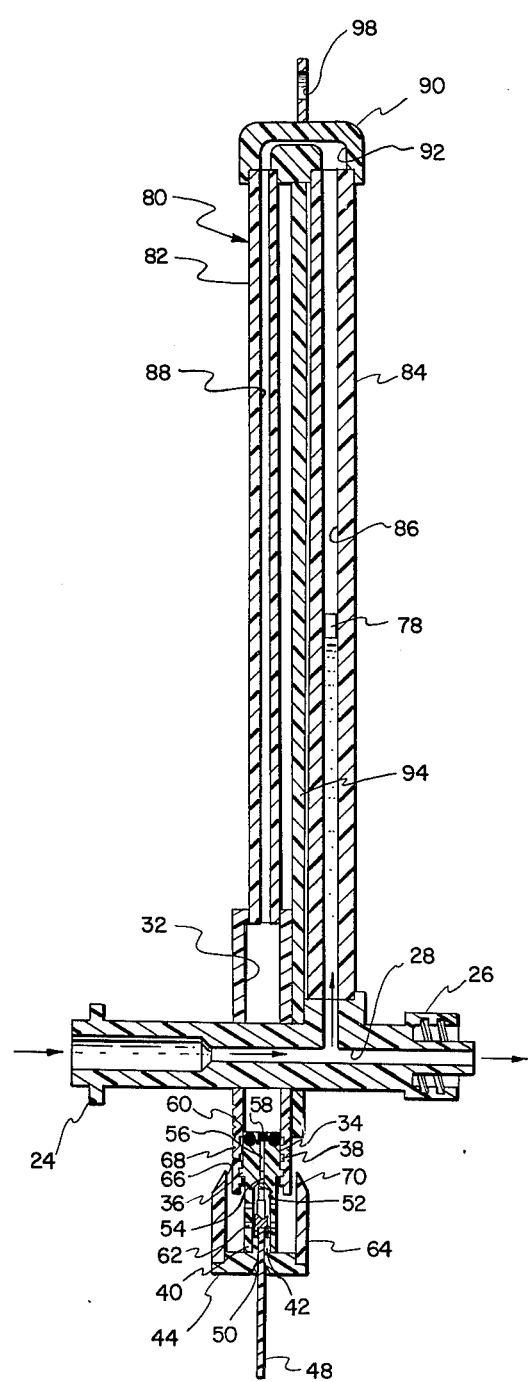
Fig. 7                    Fig. 8

MANOMETER FOR INFUSION APPARATUS

BACKGROUND

1. Field of the Invention

This invention relates to manometers for infusion apparatus and more particularly to a manometer for measuring the hydrodynamic pressure of fluids parenterally administered to a patient.

2. The Prior Art

Intravenous infusion of fluids into a patient has become a routine hospital procedure in many types of situations. Typically, the intravenous infusion apparatus consists of an indwelling catheter that is connected through tubing to a fluid source such as an elevated plastic bag.

Because of the resistance of the catheter, catheter tubing and back pressure from the patient, it is oftentimes necessary to supply a pressure source such as a pump-up pressure cuff. The pressure cuff is placed over the plastic bag containing the fluid and is inflated. In this manner the infusion fluid may be delivered at a particular pressure that is consistent with a desired flow rate for the infusion fluid.

In some types of situations it is of utmost importance to provide a carefully controlled flow rate of the infusion fluid. For example, proper administration of some types of medication may require carefully controlled flow rates over long periods of time. Since flow rate is dependent upon the hydrodynamic pressure of the infusion fluid, fluid pressures must be continuously monitored.

In the past, one of the problems associated with parenteral administration of fluids to a patient has been the problem of accurately measuring the hydrodynamic pressure of the fluid being infused into the patient. Typically it has been assumed that the pressure exerted by the pressure cuff on the fluid source bag is the same as the pressure exerted on the fluid at its point of infusion into the patient. The level of pressure at the pressure cuff is read directly from a gage that is associated with the pressure cuff.

However, in practice, the hydrodynamic pressure of the fluid being infused into the patient is not the same as the hydrostatic pressure measured at the pressure cuff. The resistance of the tubing and catheter system and the back pressure of the patient all have an effect on the hydrodynamic pressure of the fluid that is infused into the patient.

To eliminate these inaccuracies manometers have been developed that may be directly placed in the tubing line and that may be operated to temporarily interrupt the fluid flow so that hydrostatic pressure measurements may be periodically taken. See, for example, U.S. Pat. No. 3,807,389.

Although these types of in-line manometers provide more accurate pressure readings of the infusion fluid, they do not permit continuous monitoring of hydrodynamic pressures. Since they measure hydrostatic pressure, such manometers require periodic interruption of the fluid flow to obtain a pressure reading. This of course may be inconvenient in some types of situations and may even be hazardous if the required pressure level drops or rises significantly between readings, resulting in over or under infusion.

From the foregoing, it will be appreciated that what is needed in the art is an in-line manometer which may be used to continuously monitor the hydrodynamic pressure of fluids that are parenterally administered to a patient. Such an invention is illustrated and described herein.

BRIEF DESCRIPTION AND OBJECTS OF THE INVENTION

The manometer of the present invention provides for continuous, direct in-line reading of the hydrodynamic pressure of a parenterally administered fluid. The manometer has a passageway that permits continuous flow of fluid therethrough. The manometer also consists of a pressure measuring chamber. One end of the pressure measuring chamber is in fluid communication with the open passageway and the other end of the pressure measuring chamber communicates with an enclosed air space. The fluid flowing through the passageway will enter the pressure chamber and will rise to a level that is dependent upon the pressure of the fluid flowing through the open passageway. Markings are placed upon the manometer so that the hydrodynamic pressure of the fluid flowing through the open passageway may be easily determined with reference to the level of the fluid in the pressure measuring chamber.

In one embodiment of the present invention, the monometer is also provided with structure which permits the size of the enclosed air space at the end of the pressure measuring chamber to be adjusted so that the manometer may be normalized for use at any one of several altitudes. A valve is also provided so that pressure readings may be reset to zero when desired. Another embodiment of the manometer has a pressure measuring chamber which decreases in its cross-sectional area from the bottom to the top of the chamber so that pressure measurements may be read in a linear fashion.

It is therefore a primary object of the present invention to provide an improved manometer for continuous in-line measurement of the hydrodynamic pressure of fluids being parenterally administered to a patient.

Another primary object of the present invention is to provide a manometer that may be easily adjusted so that it may be normalized for use at any one of several different altitudes.

Yet another object of the present invention is to provide a manometer having a simple valve structure which may be easily and quickly opened and instantaneously closed when it is desired to obtain a zero calibration.

Yet another important object of the present invention is to provide a manometer that is configurated so as to accommodate linear reading of the hydrodynamic fluid pressure.

These and other objects and features of the present invention will become more fully apparent from the following description and appended claims taken in conjunction with the accompanying drawing.

BRIEF DESCRIPTION OF THE DRAWING

FIG. 7 is a perspective view of another embodiment of the manometer of the present invention.

FIG. 8 is a cross-sectional view of the manometer of FIG. 7 taken along lines 8—8.

DETAILED DESCRIPTION OF THE PREFERRED EMBODIMENTS

Figure 1:
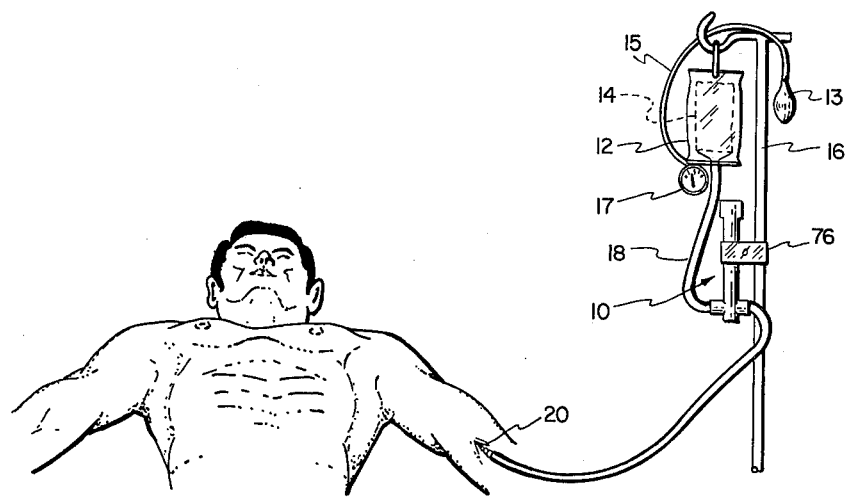
FIG. 1 is a schematic illustration showing the manometer of the present invention as used with conventional intravenous infusion apparatus.

The invention is best understood by reference to the figures wherein like parts are designated with like numerals throughout.

1. The Embodiment of FIGS. 1-3

The manometer of the present invention may be used with a variety of different types of intravenous infusion apparatus. For purposes of illustration, the manometer generally designated 10 has been shown in FIG. 1 in conjunction with a conventional pressure infusor 12 and a fluid supply bag 14. The fluid supply bag 14 is typically constructed from a flexible material and is suspended from a stand 16.

The pressure infusor 12 may consist of a pump-up pressure cuff which surrounds the fluid bag 14. Pressure cuff 12 may be inflated by pumping the bulb 13 attached to tubing 15. As pressure cuff 12 is inflated, pressure is exerted on the fluid bag 14 so as to force the flow of fluid under pressure through tubing 18. The pressure exerted by pressure cuff 12 on bag 14 is read from gage 17.

As schematically illustrated in FIG. 1, the manometer generally designated 10 may be coupled directly into the tubing 18 and may be clipped or otherwise supported on the stand 16 or, as hereinafter more fully described, manometer 10 may also be simply suspended by the tubing 18. From the manometer 10, the tubing 18 is coupled to an indwelling catheter 20 inserted into the patient.

Figure 2:
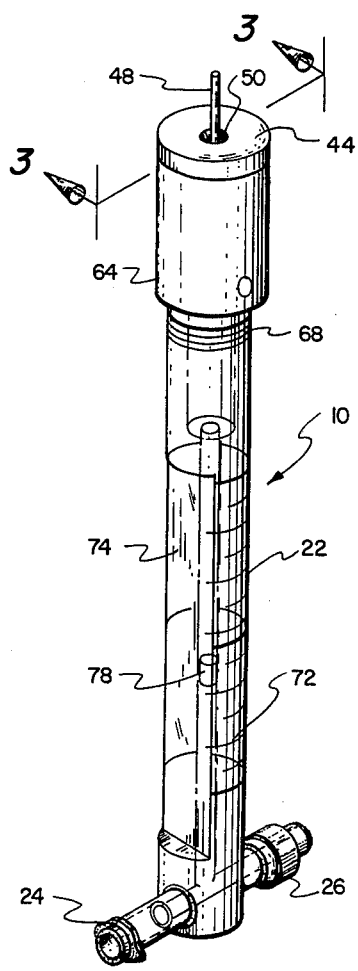
FIG. 2 is a perspective view of one embodiment of the manometer of the present invention.
Figure 3:
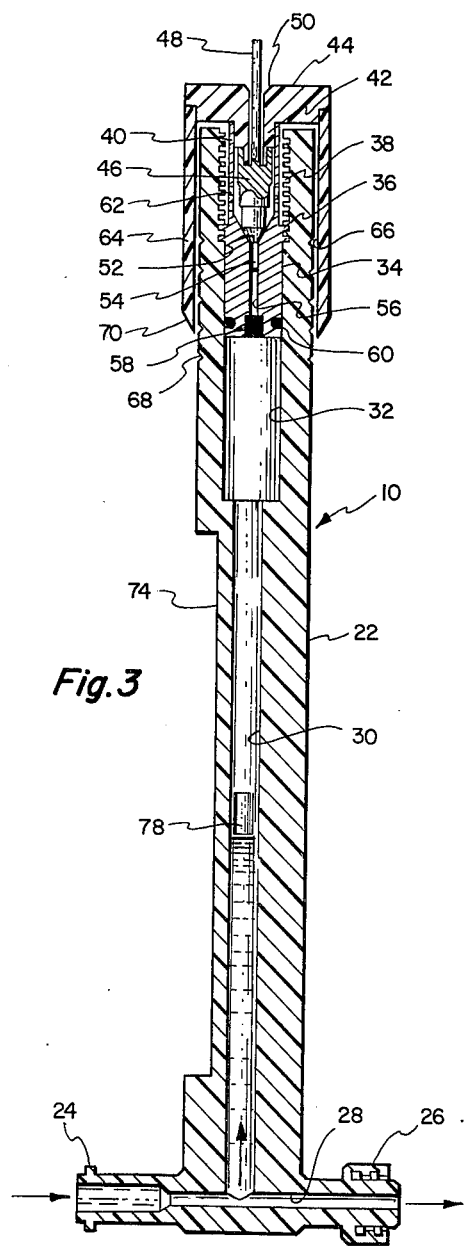
FIG. 3 is a cross section of the manometer of FIG. 1 taken along lines 3—3.

As shown best in FIGS. 2 and 3, the manometer generally designated 10 consists in part of a molded housing 22. Housing 22 is constructed from plastic or other transparent material so that the level of fluid in the manometer may be easily determined, as described below.

At the base of housing 22, a male Luer fitting 26 and a female Luer fitting 24 are provided. The female Luer fitting 24 is coupled with the portion of tubing 18 that is attached to the fluid source 14. The male Luer fitting 26 is attached to the portion of tubing 18 which leads to the patient. Female Luer fitting 24 thus provides an inlet and the male Luer fitting 26 provides an outlet for the fluid which flows through the manometer.

An open passageway 28 is formed through the housing 22 so as to provide fluid communication between the male Luer fitting 26 and the female Luer fitting 24. As hereinafter more fully described, the fluid being infused into the patient flows into the inlet at Luer fitting 24, through the open passageway 28 and out of the outlet at Luer fitting 26 into the tubing 18 that is connected to the patient.

As illustrated best in FIG. 3, a pressure measuring chamber 30 is also formed in housing 22. Pressure measuring chamber 30 extends vertically upward through housing 22 and is in fluid communication with the open passageway 28 at the base of the pressure measuring chamber 30. The top of the pressure measuring chamber 30 opens into an enlarged air space 32. Air space 32 is enclosed at its upper end by a plug 34. The upper portion of plug 34 is provided with threads as at 36 which engage corresponding threads 38 provided in the upper portion of housing 22.

The top portion of plug 34 consists of an annular sleeve 40. Annular sleeve 40 snugly fits over a shoulder 42 provided in the end cap 44. Annular sleeve 40 is cemented or otherwise securely joined to the shoulder 42. For purposes to be hereinafter more fully described, as end cap 44 is rotated in one direction the plug 34 will be inserted further into the space 32 thus decreasing space 32. As end cap 44 is rotated in the opposite direction, the plug 34 will be somewhat withdrawn thereby increasing the space 32.

A resilient valve 46 is housed within the portion of plug 34 that is surrounded by the annular sleeve 40. Valve 46 is constructed from rubber or synthetic rubber and has a valve stem 48 that extends through an opening 50 provided in the end cap 44. The tip 52 of resilient valve 46 is conically shaped so as to securely seat within a corresponding conical recess provided in the plug 34. A nipple 54 is attached at the tip 52 of valve 46 and nipple 54 projects into a throughbore 56 that extends through the center of plug 34. Nipple 54 helps to insure that valve 46 is properly seated in the conical recess.

The length of valve 46 is slightly greater than the distance from the conically shaped recess of plug 34 to the end cap 44 so that the valve 46 is sealed against the conical recess of plug 34 under its own pressure, thereby providing an airtight enclosure at the end of throughbore 56. A micron filter 58 is provided at the leading end of throughbore 56 to prevent entry of bacteria or other contaminants into the pressure measuring chamber 30. An O-ring 60 provides an airtight seal at the leading edge of plug 34 within the air space 32.

A small opening 62 is provided through the annular sleeve 40 of plug 34. End cap 44 is attached to a cylindrical sleeve 64 which extends down along a portion of the sides of housing 22. Cylindrical sleeve 64 is spaced slightly away from the sides of housing 22 so as to provide an air passageway 66 that communicates with the ambient atmosphere. As hereinafter more fully described, resilient valve 46 may be opened by pulling on the valve stem 48. When the resilient valve 46 is opened, enclosed air space 32 is vented through the throughbore 56, through the opening 62 and through the air passageway 66 to the ambient atmosphere.

In order to permit the manometer 10 to be normalized for use at any one of several different altitude levels, it is necessary to be able to adjust the size of the enclosed air space 32. For example, a higher altitude may require that the size of air space 32 be decreased. Similarly, a lower altitude may require a larger air space 32 at the end of pressure measuring chamber 30. In order to increase the size of air space 32, end cap 44 may be twisted in one direction so as to partially withdraw the leading end of plug 34 from the air space 32. Air space 32 may be decreased by twisting end cap 44 in the opposite direction so as to insert the leading end of plug 34 further into the air space 32.

As illustrated at 68, a plurality of markings may be engraved or otherwise placed on the exterior surface of housing 22 adjacent the tip 70 of cylindrical sleeve 64. Each of the markings 68 correspond to a different level of altitude. Thus, the tip 70 of cylindrical sleeve 64 may be used to indicate the position of plug 34 which corresponds to a particular size of the air space 32 for a given level of altitude.

As further illustrated in FIG. 2, a plurality of markings 72 are also engraved or painted on the portion of the housing 22 that encloses the pressure measuring chamber 30. Markings 72 correspond to hydrodynamic pressure readings of the fluid flowing through passageway 28. A portion of the exterior of housing 22 is provided with a flat recess 74 which extends along the length of housing 22 opposite the markings 72. The flat recess 74 permits the markings 72 to be easily determined with reference to the level of fluids in the pressure measuring chamber 30.

The manner of operating the manometer 10 will be readily apparent to those of ordinary skill in the art. First, the manometer is coupled at Luer fitting 24 to the portion of tubing 18 that leads to the fluid source 14. (See FIG. 1). Luer fitting 26 is then coupled to the portion of tubing 18 that leads to the catheter 20 that is inserted into the patient.

Next, the manometer 10 is normalized for use at a particular altitude. This is accomplished by twisting the end cap 44 so as to either increase or decrease the size of air space 32. The desired altitude adjustment is determined by twisting end cap 44 until the tip 70 of sleeve 64 is adjacent the marking 68 that corresponds to the desired altitude.

Once the manometer has been normalized for use at a particular level of altitude, fluid is permitted to enter the tubing 18 and manometer 10 and the pressure reading is then set to zero. This is done by raising the manometer 10 to the same level as the fluid source 14. The valve stem 48 is then pulled so as to unseat the resilient valve 46, thereby venting the enclosed air spacing 32 through the throughbore 56, opening 62 and air passageway 66 to the ambient atmosphere. When the pressure measuring chamber 30 is thus vented to the ambient atmosphere, the level of fluid contained in the pressure measuring chamber 30 will seek the zero point. The valve stem 48 is then released and the resilient valve 46 will instantaneously and automatically close, providing an airtight seal.

Thereafter, the manometer 10 may be clipped to the stand 16 with a spring clip 76 (see FIG. 1). Alternatively, the manometer 10 may be simply suspended in the tubing line 18.

The hydrodynamic pressure of the fluid flowing through the open passageway 28 may be read directly from the level of the fluid contained in the pressure measuring chamber 30. As fluid under pressure flows through the passageway 28, the resistance of the catheter 20, tubing 18 and the back pressure of the patient will cause a certain amount of the fluid to enter the pressure measuring chamber 30 and to rise to a certain level, depending upon the pressure that is exerted by the pressure cuff 12 (see FIG. 1) on the fluid source 14. As the pressure exerted on the fluid source 14 is increased, the air contained in the enclosed air space 32 will be compressed and the level of fluid in the pressure measuring chamber 30 will increase. As the pressure exerted on the fluid source 14 is decreased, the air pressure in the enclosed air space 32 will cause the level of fluid in the pressure measuring chamber 30 to correspondingly decrease. A flotation marker 78 is contained within the pressure measuring chamber 30 so that the level of fluid may be readily determined in reference to markings 72.

2. The Embodiment of FIGS. 7-8

The embodiment of the manometer illustrated at FIGS. 7 and 8 operates in the same way as the embodiment previously illustrated in FIGS. 1-3 and described above. The manometer illustrated in FIGS. 7 and 8 differs from the embodiment of FIGS. 1-3 primarily in the configuration of the housing.

As illustrated in FIGS. 7 and 8, the housing generally designated 80 consists of two elongated cylindrical members 82 and 84. The interior of cylindrical member 84 forms a pressure measuring chamber 86. Like the embodiment of FIGS. 1-3, pressure measuring chamber 86 communicates at its base with the open passageway 28 through which the infusion fluid flows.

The interior of the elongated cylindrical member 82 forms a narrow passageway 88 that communicates at its base with the enclosed air space 32. Each of the cylindrical members 82 and 84 are attached at their top to a cover 90. A connecting passageway 92 is provided in the cover 90. Thus, the pressure measuring chamber 86 communicates through connecting passageway 92 and passageway 88 with the enclosed air space 32.

As shown best in FIG. 7, a thin cardboard or plastic backing 94 is inserted between the cylindrical members 82 and 84. Markings 96 are placed on the backing 94. The markings 96 correspond to hydrodynamic pressures of the fluid flowing through passageway 28 as determined from the level of fluid in the pressure measuring chamber 86. The backing 94 is also provided at its top with a hole 98 through which a hook (not shown) may be used to suspend the manometer from a stand.

As previously indicated, the manometer illustrated in FIGS. 7 and 8 operates in essentially the same way as the embodiment of FIGS. 1-3. The manometer is connected at Luer fitting 24 to a pressurized fluid source and the Luer fitting 26 is connected to the portion of tubing that leads to the patient. As fluid flows through the open passageway 28, fluid will enter the pressure measuring chamber 86 of cylindrical member 84 and will rise to a level that is dependent upon the hydrodynamic pressure of the fluid flowing through the passageway 28. For example, as the pressure exerted on the fluid source is increased, the level of fluid in the pressure measuring chamber 86 will further compress the air contained in the enclosed air space 32 so that the level of the fluid in pressure measuring chamber 86 will rise. As the pressure exerted on the fluid source is decreased, the air pressure of the air contained in the enclosed air space 32 will force the level of fluid in the pressure measuring chamber 86 to drop.

The manometer illustrated in FIGS. 7 and 8 may be normalized for use at any one of several different altitude levels by rotating the end cap 44 in the manner previously described. Pressure readings may be set to zero by raising the manometer to the same level as the fluid source and by pulling the valve stem 48 so as to vent the enclosed air space 32 to the ambient atmosphere in the manner described above. As with the embodiment of FIGS. 1-3, the manometer illustrated in FIGS. 7 and 8 is also provided with a flotation marker 78 so that the level of fluid in the pressure measuring chamber 86 may be readily determined with reference to the markings 96 contained on the backing 94.

3. The Embodiment of FIG. 4

Figure 4:
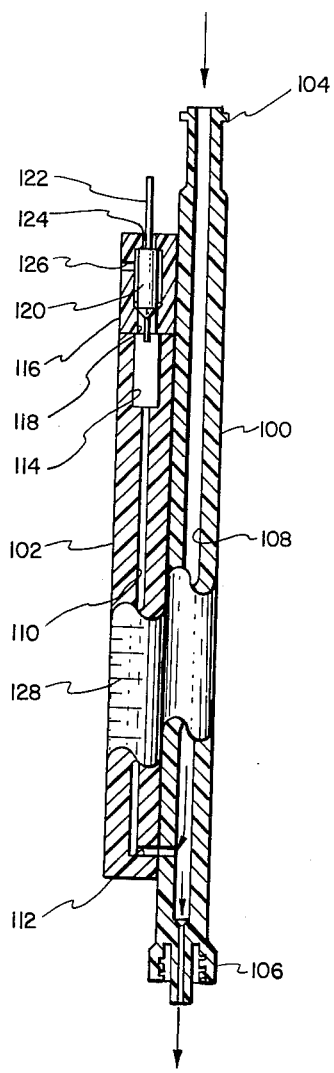
FIG. 4 is a partial cross-sectional view of a second embodiment of the manometer of the present invention.

FIG. 4 is illustrative of yet another embodiment of the manometer of the present invention. As shown in FIG. 4, the manometer consists of two adjacent cylinders 100 and 102. A Luer fitting 104 is provided at the top of cylinder 100 and a Luer fitting 106 is provided at the base of cylinder 100. The Luer fitting 104 is coupled to the portion of tubing that is attached to the fluid source and the Luer fitting 106 is attached to the portion of tubing that leads to the patient. An open passageway 108 is formed through the cylinder 100 so as to provide fluid communication between the Luer fitting 104 and the Luer fitting 106. Thus, the fluid being infused into the patient flows into the inlet at Luer fitting 104, through the open passageway 108 and out of the outlet at Luer fitting 106 into the tubing that is connected to the patient.

Cylinder 102 is situated adjacent to cylinder 100 and is cemented or otherwise rigidly attached thereto. Cylinder 102, like cylinder 100, may be molded from transparent plastic or any suitable type of transparent material so as to permit visual inspection of the fluid that enters therein.

A pressure measuring chamber 110 is formed in the interior of the cylinder 102. The base of cylinder 102 is enclosed and is provided with a connecting passageway 112 which permits fluid flowing through the open passageway 108 to enter into the pressure measuring chamber 110.

The top of pressure measuring chamber 110 opens into an enlarged air space 114. The enlarged air space 114 is enclosed by an end cap 116 that is mounted at the top of cylinder 102.

The interior of end cap 116 is provided with a throughbore 118. The upper portion of throughbore 118 is configured so as to provide a conically shaped recess which acts as a valve seat for a resilient valve 120. The resilient valve 120 is provided with a valve stem 122 that extends through an opening 124 provided through the top of end cap 116. An outlet port 126 is provided through the side of end cap 116. Thus, when the valve stem 122 is pulled, the resilient valve 120 is unseated and the enclosed air space 114 may be vented through the throughbore 118 and through the outlet port 126 to the ambient atmosphere.

As further illustrated in FIG. 4, markings 128 are placed on the exterior of cylinder 102 adjacent the pressure measuring chamber 110. Each of the markings 128 correspond to hydrodynamic pressure readings of the fluid flowing through passageway 108.

Unlike the embodiments of the manometer previously described, the manometer illustrated in FIG. 4 does not show structure which permits the size of the enclosed air space 114 to be adjusted for purposes of normalizing the manometer for use at different altitudes. It will therefore be appreciated that the size of the enclosed air space 114 would have to be specifically constructed for one particular altitude. However, it will of course be recognized that the embodiment of the invention illustrated at FIG. 4 could also be provided with any suitable type of structure which would permit the size of the enclosed air space 114 to be adjusted so as to accommodate use of the manometer at any of several different altitudes.

As with the previous embodiments, the manner of using the manometer illustrated in FIG. 4 will be readily apparent to those of ordinary skill in the art. The manometer is coupled directly into the tubing by attaching the tubing which leads to the fluid source at Luer fitting 104 and by attaching the tubing that leads to the patient to Luer fitting 106. Fluid is permitted to fill the tubing and enter the manometer and the pressure reading is then set to zero by raising the manometer to the same level as the fluid source and pulling the valve stem 122 so as to vent the enclosed air space 114 through the throughbore 118 and outlet port 126 to the ambient atmosphere. The valve stem 122 is then released so that resilient valve 120 is reseated, providing an airtight seal for the air space 114.

As fluid under pressure flows through the passageway 108, the resistance of the catheter, tubing and back pressure of the patient will cause a certain amount of the fluid to enter through passageway 112 into the pressure measuring chamber 110. As described in connection with the previous embodiments, depending upon the pressure that is exerted on the fluid source, the level of fluid in the pressure measuring chamber 110 will rise to a particular level which may be read in reference to the markings 128 provided on the exterior of cylinder 102. In this manner, the hydrodynamic pressure of the fluid flowing through passageway 108 may be continuously monitored.

4. The Embodiments of FIGS. 5 and 6

Figure 5:
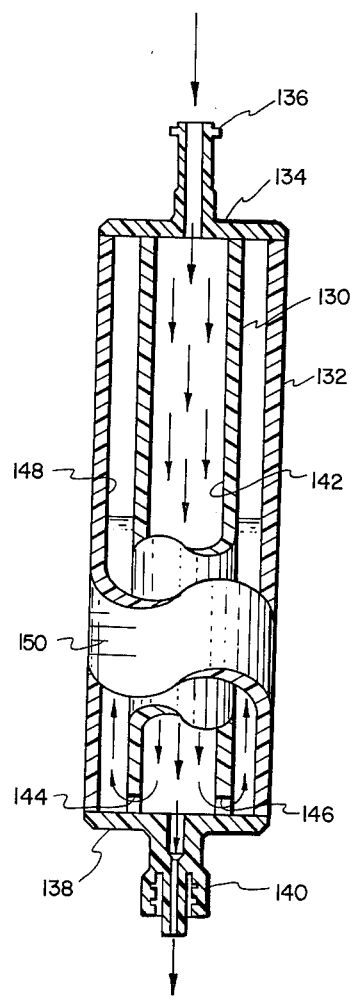
FIG. 5 is a partial cross-sectional view of a third embodiment of the manometer.

The embodiment of the manometer illustrated in FIG. 5 is similar in construction and operation to the embodiment illustrated and described in connection with FIG. 4. As shown in FIG. 5, the manometer consists of a first hollow cylinder 130 and a second hollow cylinder 132 that is concentrically spaced from and that circumscribes the first cylinder 130. As with the previous embodiments, cylinders 130 and 132 are molded from transparent plastic or other suitable transparent material so as to permit visual inspection of the fluid flowing therethrough.

The top of cylinders 130 and 132 are enclosed by an end cap 134. End cap 134 is provided with a Luer fitting 136 that may be connected to the tubing which leads to the fluid source in the manner previously described. The bottom of cylinders 130 and 132 are similarly enclosed by an end cap 138 that is provided with a Luer fitting 140. Luer fitting 140, as in the previous embodiments, is attached to the tubing that leads to the patient.

The hollow of cylinder 130 provides a passageway 142 through which fluid may flow from the inlet at Luer fitting 136 to the outlet at Luer fitting 140. Openings 144 and 146 are provided at the base of cylinder 130 so as to permit fluid communication from the passageway 142 to the pressure measuring chamber 148 defined by the space between cylinders 130 and 132. Thus, the fluid flowing through the passageway 142 will enter the pressure measuring chamber 148 through openings 144 and 146.

Since the pressure measuring chamber 148 is enclosed by the end cap 134, the top portion of pressure measuring chamber 148 provides an enclosed air space. Thus, as described with the previous embodiments, the level of fluid entering the pressure measuring chamber 148 will be dependent upon the hydrodynamic pressure of the fluid flowing through passageway 142 and will vary in relation to the pressure exerted at the fluid source. Markings 150 provided on the exterior of cylinder 132 may be used for purposes of reading the hydrodynamic pressure as determined with reference to the level of fluid in the pressure measuring chamber 148.

It will also be noted from FIG. 5 that the concentric arrangement of cylinders 130 and 132 provide symmetry about the vertical axis. The symmetrical configuration of the manometer illustrated in FIG. 5 is advantageous because it prevents tilting of the manometer when it is vertically suspended in the tubing and is thus always easy to read. Moreover, it will of course be appreciated that the manometer illustrated in FIG. 5 could be suitably modified in accordance with the teachings of the previously described embodiments so as to provide structure which would permit the pressure measuring chamber 148 to be vented and to be selectively adjusted for use at any desired altitude.

Figure 6:
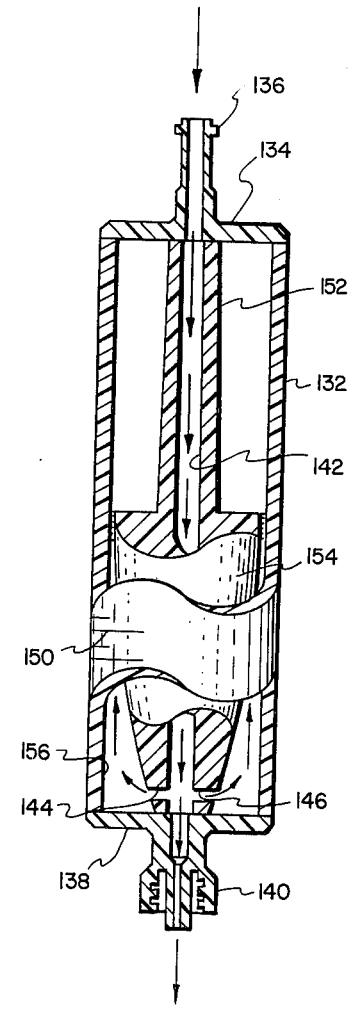
FIG. 6 is a partial cross-sectional view of a fourth embodiment of the manometer.

The embodiment of the manometer illustrated in FIG. 6 differs from the manometer illustrated in FIG. 5 only in the way in which the inner cylinder is configurated. In FIG. 6, the inner cylinder 152 is constructed so that the lower portion 154 of the cylinder 152 is parabolically shaped. The parabolic portion 154 of inner cylinder 152 thus creates a pressure measuring chamber 156 that has a progressively decreasing cross-sectional flow area from its bottom to its top.

In practice, it has been found that in a manometer of the type illustrated in FIG. 5, the level of fluid in the pressure measuring chamber 148 varies non-linearly in relation to the hydrodynamic pressure of the fluid flowing through the passageway 142. Thus, by providing a pressure measuring chamber 156 that has a progressively decreasing cross-sectional flow area from its bottom to its top, the level of fluid in the pressure measuring chamber 156 may be caused to vary in a linear fashion in relation to variations in the hydrodynamic pressure of the fluid flowing through passageway 142. In this manner, the hydrodynamic pressure of the fluid flowing through passageway 142 may be read linearly from the level of the fluid in pressure measuring chamber 156.

As with the embodiment illustrated in FIG. 5, the manometer illustrated in FIG. 6 is symmetrical about the vertical axis and the manometer will thus be balanced and will not tilt when it is vertically suspended in the tubing line.

From the foregoing, it will be appreciated that the manometer of the present invention advantageously permits continuous in-line measurement of the hydrodynamic pressure of fluids that are parenterally administered to a patient. The manometer may be adjusted so that it may be normalized for use at any of several different altitudes and it is provided with a simple valve structure that may be easily and quickly opened and that instantaneously closes when it is desired to set the pressure reading to zero. The manometer is simple in its construction and operation and is light in weight so that it may be easily suspended in the fluid line.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A manometer for measuring the hydrodynamic pressure of fluids parenterally administered to a patient, said manometer comprising:
   a housing, said housing having a fluid inlet means and a fluid outlet means;
   a continuously open passageway formed in said housing, said passageway accomodating continuous flow of fluid therethrough from said fluid inlet means to said fluid outlet means;
   a pressure measuring chamber formed in said housing, one end of said measuring chamber being in fluid communication with said passageway, said measuring chamber having at the other end thereof a normally closed air space that defines a nonexpansible volume; and
   reference means, associated with said pressure measuring chamber, for indicating the pressure of the fluid flowing through said passageway.

2. A manometer as defined in claim 1 wherein said housing is constructed from transparent material so as to permit visual inspection of the fluid flowing through said passageway and entering said pressure measuring chamber.

3. A manometer as defined in claim 1 further comprising a flotation marker contained within said pressure measuring chamber, said marker floating on top of the fluid which enters said measuring chamber so as to facilitate determination of the level of fluid contained in said measuring chamber with reference to said reference means.

4. A manometer as defined in claim 1 wherein said reference means comprise a plurality of markings placed upon said housing and from which the pressure of the fluid flowing through said passageway may be determined from the level of the fluid contained in said measuring chamber with reference to said markings.

5. A manometer as defined in claim 4 wherein at least a portion of said housing is a flat surface which facilitates reading of the markings placed upon said housing.

6. A manometer as defined in claim 1 wherein said reference means comprise an essentially flat strip of material placed adjacent said pressure measuring chamber, said strip having a plurality of markings thereon from which the pressure of the fluid flowing through said passageway may be determined from the level of the fluid contained in said measuring chamber with reference to the markings on said strip.

7. A manometer as defined in claim 1 further comprising valve means for venting said enclosed air space to the ambient air.

8. A manometer as defined in claim 1 further comprising means for adjusting the size of the enclosed air space of said pressure measuring chamber so as to permit said manometer to be normalized for use at any of a plurality of different altitudes.

9. A manometer as defined in claim 8 further comprising means for indicating the position of said adjusting means in accordance with one or more predetermined positions each of which corresponds to a setting for a different altitude.

10. A manometer as defined in claim 1 wherein said housing comprises:
    a first hollow cylinder, the hollow of said cylinder providing said passageway for continuous flow of fluid therethrough from said fluid inlet means to said fluid outlet means; and
    a second hollow cylinder concentrically spaced from and circumscribing said first cylinder so as to form said pressure measuring chamber therebetween, said first cylinder further having an outlet opening at the base thereof which provides fluid communication between said measuring chamber and said passageway.

11. A manometer as defined in claim 10 wherein each of said first and second cylinders are symmetrically configurated about the vertical axis so that the manometer will be sufficiently balanced as to prevent tilting of the manometer when vertically hung.

12. A manometer as defined in claim 10 wherein at least a portion of the exterior of said first cylinder is configurated so as to permit linear reading of the fluid which enters said pressure measuring chamber.

13. A manometer as defined in claim 1 wherein said housing comprises:
   a first hollow cylinder, the hollow of said first cylinder providing said passageway for continuous flow of fluid therethrough from said fluid inlet means to said fluid outlet means; and
   a second hollow cylinder adjacent to said first hollow cylinder, the hollow of said second cylinder providing said pressure measuring chamber, and said first and second cylinders having at the base thereof a connecting opening for providing fluid communication between said passageway and said pressure measuring chamber.

14. A manometer for measuring the hydrodynamic pressure of fluids parenterally administered to a patient, said manometer comprising:
   a housing, said housing having a fluid inlet means and a fluid outlet means;
   a continuously open passageway formed in said housing, said passageway accomodating continuous flow of fluid therethrough from said fluid inlet means to said fluid outlet means;
   a pressure measuring chamber formed in said housing, one end of said measuring chamber being in fluid communication with said passageway and said pressure measuring chamber having at the other end thereof an enclosed air space that defines a non-expansible volume;
   reference means, associated with said pressure measuring chamber, for indicating the pressure of the fluid flowing through said passageway; and
   means for adjusting the size of said enclosed air space so as to permit said manometer to be normalized for use at any of a plurality of different altitudes.

15. A manometer as defined in claim 14 further comprising valve means for venting said enclosed air space to the ambient air.

16. A manometer as defined in claim 15 wherein said means for adjusting the size of said enclosed air space comprise a screw engaged in at least a portion of said enclosed air space, said screw having a throughbore therein so as to permit said enclosed air space to be vented when said valve means are opened.

17. A manometer as defined in claim 16 further comprising means for visually indicating the position of said screw in accordance with one or more predetermined positions each of which corresponds to a setting for a different altitude.

18. A manometer as defined in claim 17 further comprising a bacteria filter interposed in the throughbore of said screw.

19. A manometer as defined in claim 18 further comprising means for sealing the leading end of said screw in fluid tight relation within said enclosed air space.

20. A manometer as defined in claim 14 wherein said housing is constructed from transparent material so as to permit visual inspection of the fluid flowing through said passageway and entering said pressure measuring chamber.

21. A manometer as defined in claim 20 wherein said reference means comprise a plurality of markings placed upon said transparent housing and from which the pressure of the fluid flowing through said passageway may be determined from the level of the fluid contained in said measuring chamber with reference to said markings.

22. A manometer as defined in claim 21 wherein at least a portion of said housing is a flat surface which facilitates reading of said markings placed upon said housing.

23. A manometer as defined in claim 22 further comprising a flotation marker contained within said pressure measuring chamber, said marker floating on top of the fluid which enters said measuring chamber so as to facilitate determination of the level of fluid contained in said measuring chamber with reference to said markings.

24. A manometer as defined in claim 23 further comprising means for vertically suspending said manometer.

25. A manometer as defined in claim 14 wherein the passageway formed in said housing is disposed at right angles to the pressure measuring chamber formed in said housing.

26. A manometer for measuring the hydrodynamic pressure of fluids parenterally administered to a patient, said manometer comprising:
   a housing, said housing having a fluid inlet means and a fluid outlet means;
   a continuously open passageway formed in said housing, said passageway accomodating continuous flow of fluid therethrough from said fluid inlet means to said fluid outlet means;
   a pressure measuring chamber formed in said housing, one end of said measuring chamber being in fluid communication with said passageway, said measuring chamber having at the other end thereof an enclosed air space that defines a non-expansible volume;

reference means, associated with said pressure measuring chamber, for indicating the pressure of the fluid flowing through said passageway;
a screw engaged in at least an upper portion of said enclosed air space, said screw having a throughbore therein and being adjustable so as to selectively enlarge or decrease the size of said enclosed air space, thereby permitting said manometer to be normalized for use at any of a plurality of different altitudes;
   means for sealing the leading end of said screw in fluid tight relation within said enclosed air space;
   filter means interposed in the throughbore of said screw;
   valve means for venting the enclosed air space of said pressure measuring chamber through said throughbore to the ambient air when said valve means are opened; and
   screw adjustment indicator means for indicating the position of said screw in relation to one or more predetermined positions each of which correspond to a setting for a different altitude.

27. A manometer for measuring the hydrodynamic pressure of fluids parenterally administered to a patient, said manometer comprising:
   (1) a housing, said housing comprising:
      a fluid inlet means and fluid outlet means;
      a first hollow cylinder, the hollow of said cylinder providing a continuously open passageway for continuous flow of fluid therethrough from said fluid inlet means to said fluid outlet means; and a second hollow cylinder concentrically spaced from and circumscribing said first cylinder so as to form a normally closed pressure measuring chamber defined by a non-expansible volume therebetween, said first cylinder having an outlet opening at the base thereof which provides fluid communication between said pressure measuring chamber and said passageway; and (2) reference means, associated with said pressure measuring chamber, for indicating the pressure of the fluid flowing through said passageway.

28. A manometer as defined in claim 27 wherein each of said first and second cylinders are symmetrically configured about the vertical axis so that the manometer will be sufficiently balanced as to prevent tilting of the manometer when vertically hung.

29. A manometer as defined in claim 28 wherein at least a portion of said housing comprising said second cylinder is constructed from transparent material so as to permit visual inspection of the fluid entering said pressure measuring chamber.

30. A manometer as defined in claim 29 wherein said reference means comprise a plurality of markings placed upon said housing so as to be readable through the transparent portion of said housing and from which the pressure of the fluid flowing through said passageway may be determined from the level of the fluid contained in said measuring chamber with reference to said markings.

31. A manometer as defined in claim 30 wherein at least a portion of the exterior of said first cylinder is parabolically configured so as to permit linear reading of the fluid which enters said pressure measuring chamber.

32. A manometer for measuring the hydrodynamic pressure of fluids parenterally administered to a patient, said manometer comprising:

(1) a housing, said housing comprising:
fluid inlet means and fluid outlet means;
a first hollow cylinder, the hollow of said first cylinder providing a continuously open passageway for continuous flow of fluids therethrough from said fluid inlet means to said fluid outlet means; and
a second hollow cylinder adjacent to said first hollow cylinder, the hollow of said second cylinder providing a normally closed pressure measuring chamber defined by a non-expansible volume, and said first and second cylinders having at the base thereof a connecting opening for providing fluid communication between said passageway in said pressure measuring chamber;

(2) reference means, associated with said pressure measuring chamber, for indicating the pressure of the fluid flowing through said passageway; and (3) valve means for venting said pressure measuring chamber to the ambient air.

33. A manometer as defined in claim 32 wherein at least the portion of said housing comprising said second cylinder is constructed from transparent material so as to permit visual inspection of the fluid entering said pressure measuring chamber.

34. A manometer as defined in claim 33 wherein said reference means comprise a plurality of markings placed upon said second cylinder and from which the pressure of the fluid flowing through said passageway may be determined from the level of the fluid contained in said measuring chamber with reference to said markings.

35. A manometer as defined in claim 34 further comprising a flotation marker contained within said pressure measuring chamber, said marker floating on top of the fluid which enters said pressure measuring chamber so as to facilitate determination of the level of fluid contained in said chamber with reference to said markings.

* * * * *